United States Patent
Bonafini et al.

(10) Patent No.: US 11,795,342 B2
(45) Date of Patent: Oct. 24, 2023

(54) BIOCOMPATIBLE POLYMERIC COATING CONTAINING THERAPEUTIC AGENTS

(71) Applicant: Acuity Polymers, Inc., Rochester, NY (US)

(72) Inventors: James A. Bonafini, Kendall, NY (US); Wayne Thomas Ferrar, Fairport, NY (US)

(73) Assignee: Acuity Polymers, Inc., Rochester, NY (US)

(*) Notice: Subject to any disclaimer, the term of this patent is extended or adjusted under 35 U.S.C. 154(b) by 0 days.

(21) Appl. No.: 16/791,429

(22) Filed: Feb. 14, 2020

(65) Prior Publication Data

US 2020/0263051 A1 Aug. 20, 2020

Related U.S. Application Data

(60) Provisional application No. 62/806,336, filed on Feb. 15, 2019.

(51) Int. Cl.
C09D 133/14 (2006.01)
A61K 47/32 (2006.01)
(Continued)

(52) U.S. Cl.
CPC ............ C09D 133/14 (2013.01); A61K 47/32 (2013.01); C09D 143/02 (2013.01); G02B 1/18 (2015.01)

(58) Field of Classification Search
CPC ........... A61L 31/10; A61K 9/00; A61K 47/32; C09D 133/14
See application file for complete search history.

(56) References Cited

U.S. PATENT DOCUMENTS 6,534,559 B1 3/2003 Vanderlaan et al.
7,815,922 B2 * 10/2010 Chaney .................. A61L 31/16
424/400

(Continued)

FOREIGN PATENT DOCUMENTS

CN 1243846 A 2/2000
JP 2008500104 1/2008
(Continued)

OTHER PUBLICATIONS

Kwangwoo Nam, et al.; "Physical and biological properties of collagen-phospholipid polymer hybrid gels"; Division of Biofunctional Molecules, Institute of Biomaterials and Bioengineering, Tokyo Medical and Dental University, Feb. 3, 2010 Kanda-Surugadai, Chiyoda-ku, Tokyo 101-0062, Japan; Biomaterials 28 (2007) 3153-3162; Received Dec. 6, 2006; accepted Mar. 8, 2007; Available online Mar. 14, 2007.

(Continued)

Primary Examiner — Dah-Wei D. Yuan
Assistant Examiner — Andrew J Bowman
(74) Attorney, Agent, or Firm — Woods Oviatt Gilman LLP; Katherine H. McGuire, Esq.

(57) ABSTRACT

A method of preparing a biocompatible polymeric coating includes preparing an aqueous polymer solution by contacting and reacting methacrylic acid and at least one methacrylate or phosphorylcholine. The methacrylate or phosphorylcholine may include hydroxyethyl methacrylate, polyethylene glycol monomethacrylate, or methacryloyloxyethyl phosphorylcholine. An aqueous coupling agent solution is prepared and is either applied to the substrate surface or is mixed with the polymer solution to form a coating solution. If the coupling agent solution was first applied to the substrate surface, the polymer solution is then applied to the primed substrate surface. Alternatively if a (Continued)

coating solution was created, the coating solution is applied to the substrate surface. In either event, the polymer solution and coupling agent solution react with the substrate to form the biocompatible polymeric coating on the substrate surface.

9 Claims, 8 Drawing Sheets

(51) Int. Cl.
*C09D 143/02* (2006.01)
*G02B 1/18* (2015.01)

(56) References Cited

U.S. PATENT DOCUMENTS

| | | |
|---|---|---|
| 9,011,831 B2 | 4/2015 | Ding |
| 9,468,706 B2 | 10/2016 | Glauser et al. |
| 2009/0053391 A1 | 2/2009 | Ludwig et al. |
| 2010/0072642 A1 | 3/2010 | Broad et al. |
| 2014/0088259 A1 | 3/2014 | Liu et al. |
| 2015/0328375 A1* | 11/2015 | Glauser .......... A61L 31/10 424/426 |
| 2016/0083610 A1 | 3/2016 | Lin et al. |

FOREIGN PATENT DOCUMENTS

| | | |
|---|---|---|
| JP | 2016526060 | 6/2017 |
| JP | 2019501270 | 1/2019 |
| WO | 2005/014698 | 2/2005 |

OTHER PUBLICATIONS

Horie, T. et al.; Differentiation function of embryotic stem cell inducible bio-interface patterned by photo-reactive phospholipid polymer. Transactions of the Materials Research Society of Japan, Dec. 31, 2008, vol. 33, No. 3, pp. 811-814.

Transactions of Materials Research Society of Japan, 2011, vol. 36, No. 4, pp. 573-576.

* cited by examiner

BIOCOMPATIBLE POLYMERIC COATING CONTAINING THERAPEUTIC AGENTS

CROSS REFERENCE TO RELATED APPLICATIONS

This application claims the benefit of U.S. provisional patent application Ser. No. 62/806,336 filed Feb. 15, 2019, and entitled "BIOCOMPATIBLE POLYMERIC COATING CONTAINING THERAPEUTIC AGENTS," the contents of which are fully incorporated herein.

TECHNICAL FIELD

The present invention relates to biocompatible polymer coatings, and more particularly to biocompatible polymer coatings containing therapeutic agents, and even more particularly to biocompatible polymer coatings exhibiting extended, controlled-release of contained therapeutic agents.

BACKGROUND OF THE INVENTION

The present invention discloses a biocompatible polymer coating and a method of producing the coating for use on such items as medical and implantable devices including, without limitation and by way of example, intraocular lenses, heart valves, wire electrical leads, catheters and the like. In a further example, the biocompatible coating may be used in conjunction with wound dressings or may itself operate as a wound care dressing or bandage contact lens. The biocompatible coating may further be functionalized to include one or more therapeutic agents within the polymer matrix or covalently bonded to the polymer network. Timed release of these therapeutic agents may also be realized through selective chemistries of the polymer network. In one aspect of the invention, the biocompatible coating comprises a water-compatible milieu and may be applied to a substrate at room temperature with reaction times less than about 10 minutes.

SUMMARY OF THE INVENTION

In accordance with an aspect of the present invention, a method of preparing a biocompatible polymeric coating comprises preparing an aqueous copolymer solution by: contacting and reacting methacrylic acid (MAA) and at least one of hydroxyethyl methacrylate (HEMA), polyethylene glycol monomethacrylate (PEGMA), and methacryloyloxyethyl phosphorylcholine (MPC) to form a polymer solution; preparing an aqueous coupling agent solution; and mixing and reacting the polymer solution with the coupling agent solution to form the coating solution. The coating solution may then be applied to a substrate surface. In one aspect of the present invention, the coupling agent within the coupling agent solution may be one or more of polyaziridine, azetidinium functionalized water soluble polymers, a water soluble carbodiimide, a diisocyanate or an isocyanate polymer.

In an additional embodiment of the present invention, a method of applying a biocompatible polymeric coating to a substrate surface comprises: preparing an aqueous polymer solution by contacting and reacting methacrylic acid (MAA) and at least one methacrylate or phosphorylcholine, such as but not limited to hydroxyethyl methacrylate (HEMA) polyethylene glycol monomethacrylate (PEGMA), and methacryloyloxyethyl phosphorylcholine (MPC); preparing an aqueous coupling solution containing one or more of polyaziridine, a water soluble carbodiimide, a diisocyanate, or a isocyanate polymer; mixing the polymer solution with the coupling solution to form a coating solution; and contacting and reacting the coating solution with a substrate surface to cover the substrate with the biocompatible polymeric coating. In one aspect of the present invention, the water soluble carbodiimide solution comprises 1-Ethyl-3-(3'-dimethylaminopropyl)carbodiimide (EDAC) and the diisocyanate comprises one or more of toluene diisocyanate, methylene diphenyl diisocyanate and hexamethylene diisocyanate.

Further steps may include loading the polymer solution in a first syringe prior to the mixing step and loading the coupling agent solution in a second syringe prior to the mixing step. The mixing step may include dispensing a first volume of polymer solution from the first syringe and dispensing a second volume of coupling agent solution from the second syringe. In one aspect of the present invention, the first syringe and the second syringe may comprise a dual cartridge syringe and the first volume may be selected to be the same as the second volume or the solutions may be dispensed in a ratio optimized for favorable reaction to the substrate.

Phosphorylcholine is a zwitterionic head group based on phosphatidylcholine in mammalian cell membranes. It is incorporated into an acrylate monomer that copolymerizes to make biological coatings. The comonomers are often hydrophobic in nature. PMB30 consists of 30 mole % MPC and 70 mole % n-butylmethacrylate and can be dip coated on various substrates for biological applications.

The incorporation of phosphorylcholine into ophthalmic materials has been a goal of several inventions. MPC has been incorporated into hydroxyethylmethacrylate (HEMA) hydrogels up to 20 wt %. However, the amount of MPC incorporated into silicon hydrogels is low due to incompatibility with silicone monomers and polymers used to make the lenses. Silicon hydrogels are advantageous because they have higher oxygen permeability than standard hydrogels. Various methods have been proposed to increase the levels of MPC in silicon containing lenses, but none have been satisfactory for achieving the high levels of MPC necessary to prevent protein deposition while at the same time being covalently bonded to the surface.

Coatings for this invention are based on a tert-polymer of 2-methacryloyloxy phosphorylcholine (MPC), poly(ethylene glycol)methylether methacrylate (MAPEG), and methacrylic acid (MAA). The coating is covalently bonded to the lens surface by the reaction of the primer containing active strained rings that bind to both the acrylic acid groups incorporated in the contact lens and the acrylic acid groups of the MPC tert-polymer coating.

We found that the polymer was insoluble in nonpolar solvents when the phosphorylcholine composed half the weight of the material. This is an important property as it reflects the dominance of the MPC units over the PEG units. Phosphorylcholine at high concentrations prevents the absorption of proteins more effectively than poly(ethylene glycol) (PEG). Proteins are also more likely to denature on a PEG surface because water is greatly influenced by the polymer chains such that the structure of the water layer can be altered on a PEG surface causing the protein to denature.

DETAILED DESCRIPTION

Figure 1:
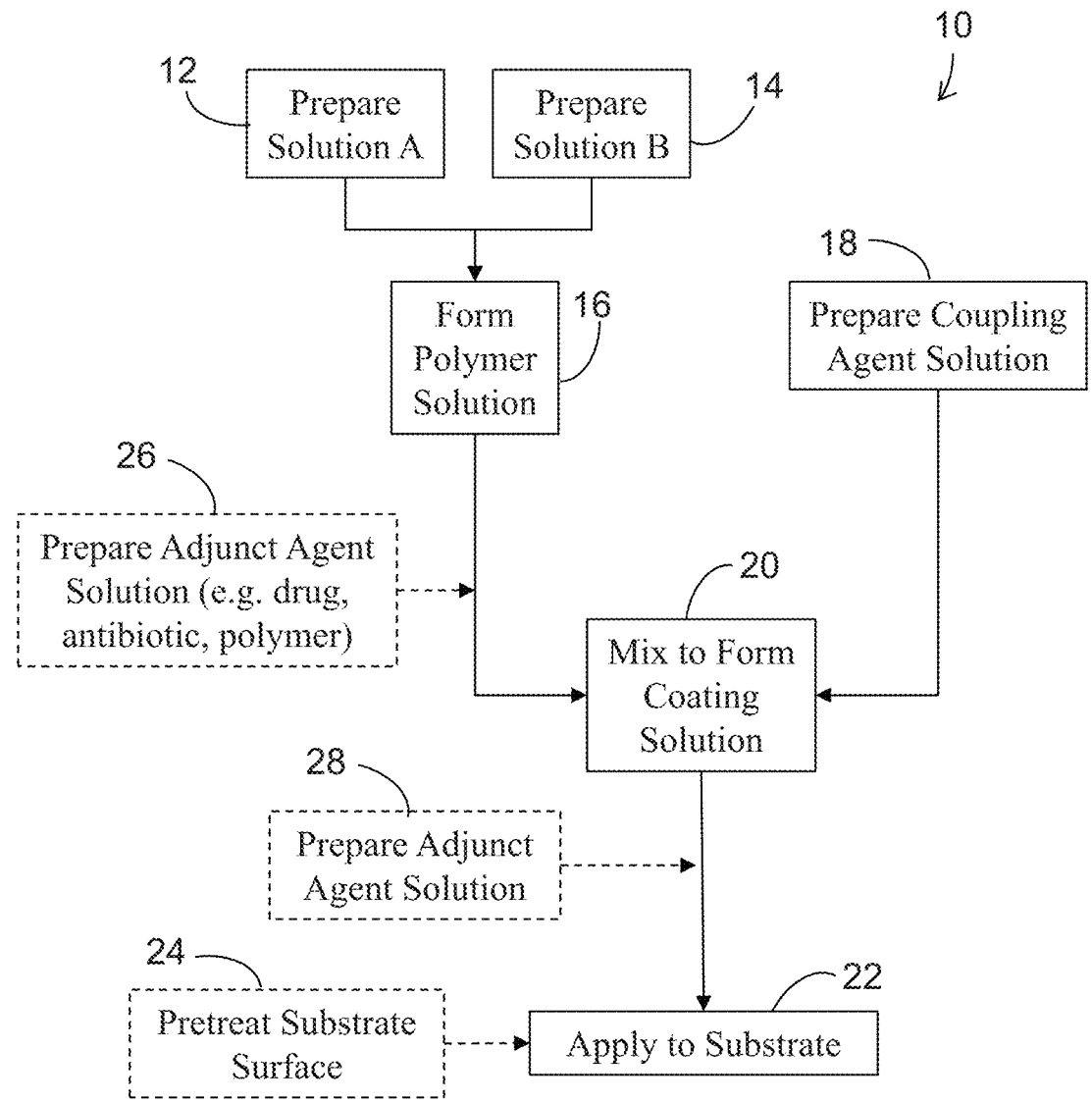
FIG. 1 is a flow chart of a method of preparing a biocompatible polymer coating in accordance with an embodiment of the present invention.

Turning now to the drawings, shown in FIG. 1 is a method 10 of preparing a biocompatible polymeric coating in accordance with an aspect of the present invention. Initially, solutions A and B are prepared in respective steps 12 and 14. Solution A includes methacrylic acid (MAA) ($C_4H_6O_2$—CAS Number 79-41-4) while solution B may include at least one methacrylate and/or phosphorylcholine, such as and without limitation to 2-hydroxyethyl methacrylate (HEMA) ($C_6H_{10}O_3$—CAS Number 868-77-9) poly(ethylene glycol) monomethacrylate (PEGMA) ($H_2C\!=\!\!C(CH_3)CO(OCH_2CH_2)_nOH$—CAS Number 25736-86-1, poly(ethylene glycol) methyl ether methacrylate (MAPEG) ($H_2C\!=\!\!C(CH_3)CO_2(CH_2CH_2O)_nCH_3$—CAS #26915-72-0), and methacryloyloxyethyl phosphorylcholine (MPC) ($C_{11}H_{22}NO_6P$—CAS Number 67881-98-5). The relative weight percentages of the constituents within each solution A and B may be selectively varied depending upon the desired characteristics of the resultant polymer coating as discussed below.

Solutions A and B are then contacted and reacted to form an aqueous copolymer solution A-B at step 16. An aqueous coupling agent solution is prepared at step 18. The coupling agent within the aqueous coupling agent solution may include, without limitation thereto, an aziridine based primer such as but not limited to polyaziridine (polyethylenimine) ($(C_2H_5N)_n$—CAS Number 9002-98-6), a carbodiimide such as 1-Ethyl-3-(3'-dimethylaminopropyl)carbodiimide) (EDAC) ($C_8H_{17}N_3$—CAS Number 25952-53-8) or a diisocyanate or isocyanate polymer. The coupling agent solution may then be contacted and reacted with copolymer solution A-B at step 20 to form a coating solution wherein the coupling agent reacts with —OH or —COOH groups within the copolymer solution to crosslink the polymer constituents of the copolymer solution and coupling agents within the coupling agent solution. Again, the choice of and weight percentage of the coupling agent may be selectively controlled so as to produce the desired polymer coating. The coating solution may then be directly applied to the substrate surface at step 22 wherein remaining reactive sites on the coupling agent may react with —OH and —COOH groups on the substrate surface.

Figure 2:
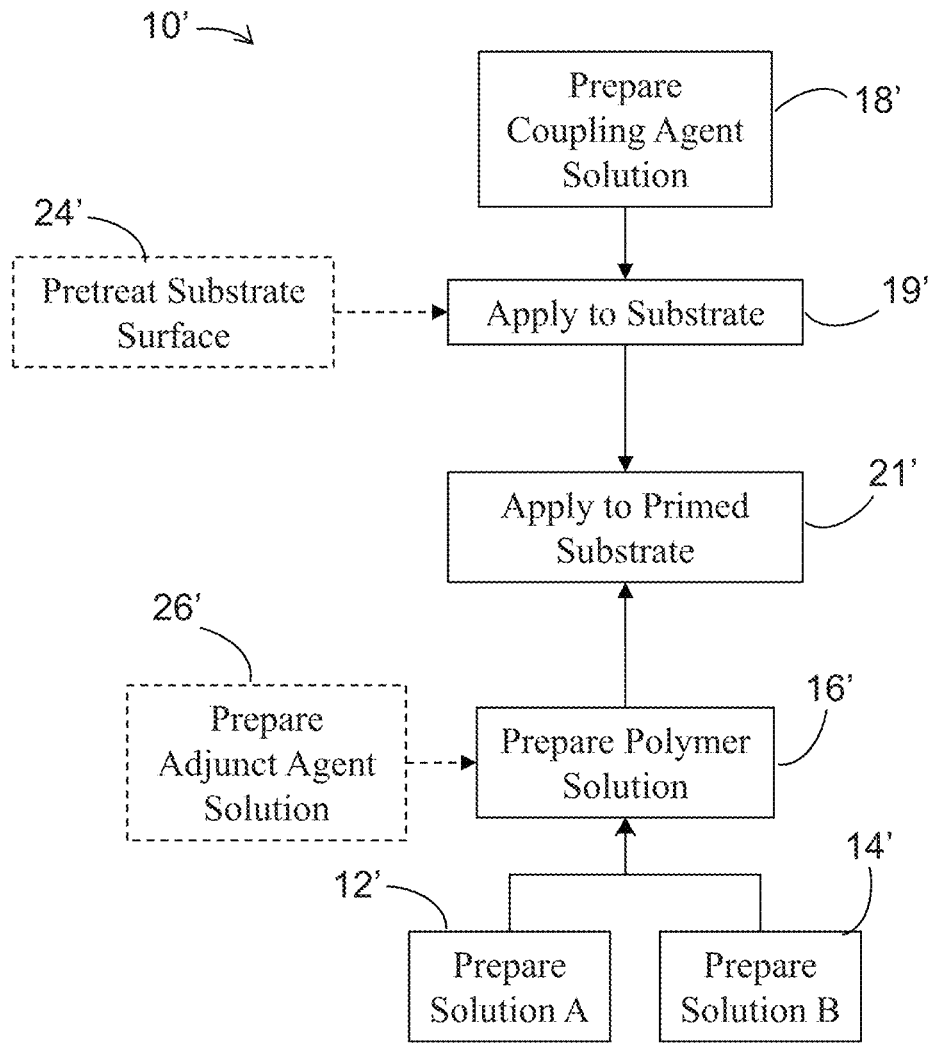
FIG. 2 is a flow chart of a method of preparing a biocompatible polymer coating in accordance with an alternative embodiment of the present invention.

In accordance with an alternative aspect of the present invention, and as shown in FIG. 2, method 10' may include preparation of solutions A and B in respective steps 12' and 14' while the aqueous coupling agent solution is prepared at step 18'. Solutions A and B may then be contacted and reacted to form an aqueous copolymer solution A-B at step 16'. However, unlike method 10 described above, the aqueous coupling agent solution may be contacted and reacted with the substrate surface at step 19' without first adding the aqueous couple agent solution to the aqueous copolymer solution A-B so as to "prime" the substrate surface. That is, the coupling agent within the coupling agent solution may react with —OH and or —COOH groups on the substrate surface so as to form a primed substrate surface suitable for reacting and crosslinking with the aqueous copolymer solution A-B. Thus, once the aqueous coupling agent solution has contacted and reacted with the substrate surface at step 19', aqueous copolymer solution A-B is then subsequently contacted and reacted with the primed substrate at step 21' so as to form the biocompatible polymeric coating.

In accordance with another aspect of the invention, the substrate may optionally undergo pretreatment at step 24 of method 10 or step 24' of method 10'. By way and without limitation thereto, a hydrophobic substrate may under plasma or acid etching pretreatments to functionalize the surface to include —OH or —COOH groups which may subsequently react with the coupling agent within the coupling agent solution as described above.

In a further aspect of the invention, one or more adjunct/therapeutic agents may be incorporated within or be covalently bonded to the biocompatible polymer network. Non-limiting examples of therapeutic agents include anti-inflammatory agents, anti-coagulants, styptic or other hemostatic agents or analgesics. The release of the therapeutic agent(s) from the biocompatible polymer coating may be selectively controlled through tailoring of the specific properties of the biocompatible polymer, such as through varying the ratios of the reagents in solutions A and B and the concentration of the coupling agent within the coupling agent solution. The therapeutic agents may be added and reacted at various times within method 10, 10'. For example, the therapeutic agents may be added to the copolymer solution at step 26, 26' and prior to step 20, 21'. Alternatively, the therapeutic agent solution may be mixed with the coating solution at step 28 and following the mixing and reaction of the polymer solution and the coupling agent solution in method 10.

In accordance with another aspect of the present invention, copolymer solution A-B may comprise an aqueous solution having a weight percent of polymer in the range of about 0.5 to about 10% by weight. This weight percentage may be made up of equal parts solution A and solution B, or may contain unequal parts depending upon the desired properties of the resultant coating solution. Thus, the composition of the polymer solution may be selectively controlled depending upon the intended end-use application.

Figure 3:
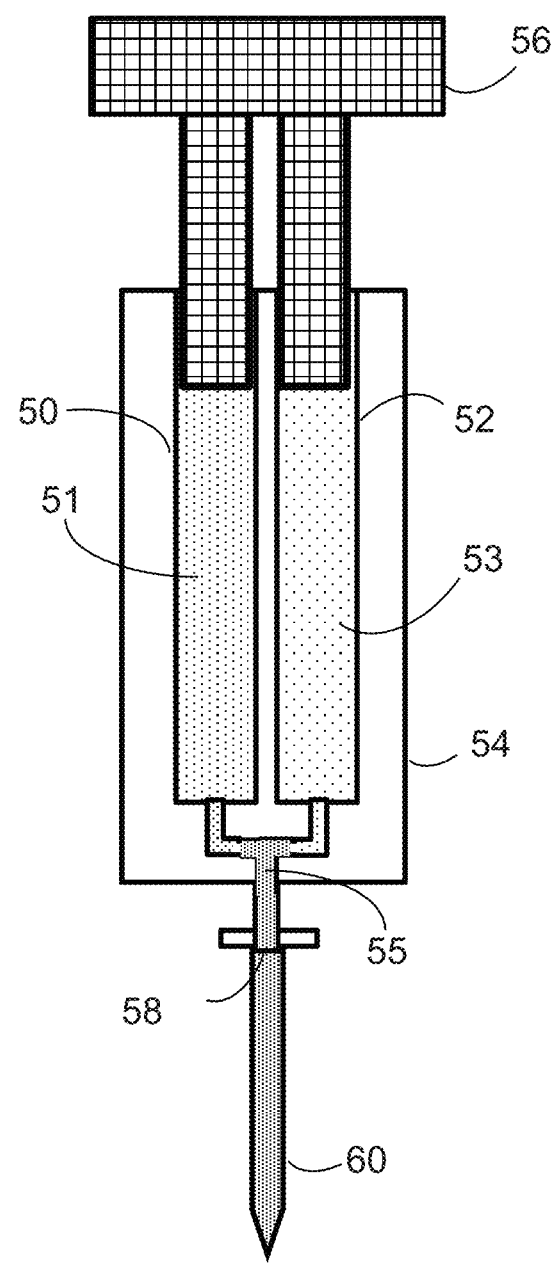
FIG. 3 is a schematic cross section view of a dual cartridge syringe suitable for use within the method of preparing a biocompatible polymer coating shown in FIGS. 1 and 2.

In accordance with an aspect of the invention, the aqueous polymer solution, coupling agent solution and/or therapeutic agent solution may be loaded within respective syringes. Each solution may then be controllably dispensed from its respective syringe for mixing and reacting to form the coating solution. As shown in FIG. 3, in one aspect, polymer solution 51 and coupling agent solution 53 are loaded within respective cartridges 50, 52 of a dual cartridge syringe 54 having a common plunger 56. Depressing of the plunger 56 thereby expels a volume of polymer solution 51 and coupling agent solution 53 (note that the weight percentages of each constituent may be the same or different, as desired, as described above). The combined solutions 55 may then mix and react within syringe outlet 58 and/or pipette tip 60 mounted onto the syringe outlet 58 of dual cartridge syringe 54. This mixing promotes reactions between the solutions so as to enable crosslinking of the coupling agent solution with —OH and/or —COOH groups of the copolymer as described above. The reacted solution may be dispensed directly onto the substrate surface.

In accordance with an aspect of the present invention, each of the solutions may be mixed and reacted at room temperature. Reaction times may be on the order of a few seconds to up to about 5 minutes, with typical reactions being completed within about 1 minute. After the coating solution or coating solution/carbodiimide solution or coating solution/carbodiimide solution/therapeutic agent solution has been contacted and reacted with the substrate surface to bind the coating solution (and optional therapeutic agents) to the substrate, remaining unreacted reagents may then be washed away from the coated substrate using clean water.

Although the invention has been described with reference to preferred embodiments thereof, it is understood that various modifications may be made thereto without departing from the full spirit and scope of the invention as defined by the claims which follow.

EXAMPLES

New hydrophilic coatings are being developed for application to contact lenses from aqueous solutions. The new polymers are based on poly(ethylene oxide) that is crosslinked onto an aziridine based primer. MPC monomer was incorporated at various percentages. We found that the polymers with greater than 60 wt % MPC had much better wetting characteristics. These polymers were also found to be insoluble in acetone and could be precipitated to give clear solids. The solid polymers could be re-dissolved in polar solvents such as alcohols or water. The polymers with lower MPC content were soluble in acetone.

TABLE 1

| Example | Ex 5 | Ex 4 | Ex 3 | Ex 2 | Ex 1 | Comp 1 | Comp 2 |
|---|---|---|---|---|---|---|---|
| "Percent MPC" Component (g) | 100 | 80 | 60 | 40 | 20 | 0 | 20 |
| PEG-Methacrylate | 0 | 1 | 2 | 3 | 4 | 5 | 0 |
| Methacrylic acid | 0.25 | 0.25 | 0.25 | 0.25 | 0.25 | 0.25 | 0 |
| methacrylic PC (MPC) | 5 | 4 | 3 | 2 | 1 | 0 | 1 |
| Polyethylene oxide MW1000 | 0 | 0 | 0 | 0 | 0 | 0.3 | 0 |
| HEMA | 0 | 0 | 0 | 0 | 0 | 0 | 4 |
| Water | 94.7 | 94.7 | 94.7 | 94.7 | 94.7 | 94.4 | 94.9 |
| 4,4' Cyano-valeric acid | 0.04 | 0.04 | 0.04 | 0.04 | 0.04 | 0.04 | 0.04 |
| sum | 99.99 | 99.99 | 99.99 | 99.99 | 99.99 | 99.99 | 99.94 |

TABLE 1-continued

[Chemical structures shown for MPC, PEG, MAA, and HEMA monomers]

Three polymers were prepared in water using a Vazo initiator. The polymers contained roughly 20, 40, 60, 80, 100 wt % HEMA-PC, more commonly referred to as MPC (2-methacyloyl oxyethyl phosphorylcholine). The other complementary monomer is MAPEG, where the PEG has a number average molecular weight ($M_n$) of 500 AMU. All the polymers contain 5 wt % methacrylic acid for crosslinking with the aziridine based primer. See Table 1, above. The polymer containing aqueous solutions were clear and viscous. There was no sign of gelling on standing, as viscosity reading remained constant over time. (Table 2).

Two control coating were also prepared. Comparative Example 1 was composed of all PEG side groups off the methacrylate backbone except for the acrylic acid moieties. The solution properties were similar to the MPC polymers of Examples 1-5.

Comparative Example 2 was made in a similar manner with 80 wt % HEMA and 20 wt % MPC. The resulting product was an opaque gel.

Brookfield Viscometer

The polymer solutions were characterized by viscosity using a Brookfield viscometer with a cone spindle at 60° C. The viscosity increased slightly with increasing MPC content. The viscosity appeared not to change upon storage of the polymer solution after 18 or 120 days.

TABLE 2

| | Ex 5 | Ex 4 | Ex 3 | Ex 2 | Ex 1 | Comp 1 | Comp 2 |
|---|---|---|---|---|---|---|---|
| initial | 54.7 | 54.7 | 48.4 | 47.0 | 44.4 | 38.5 | 43.6 |
| 18 days | | | | 45.0 | 43.8 | | |
| 120 days | | 49.6 | | | | | |

Water Contact Angle

Figure 4:
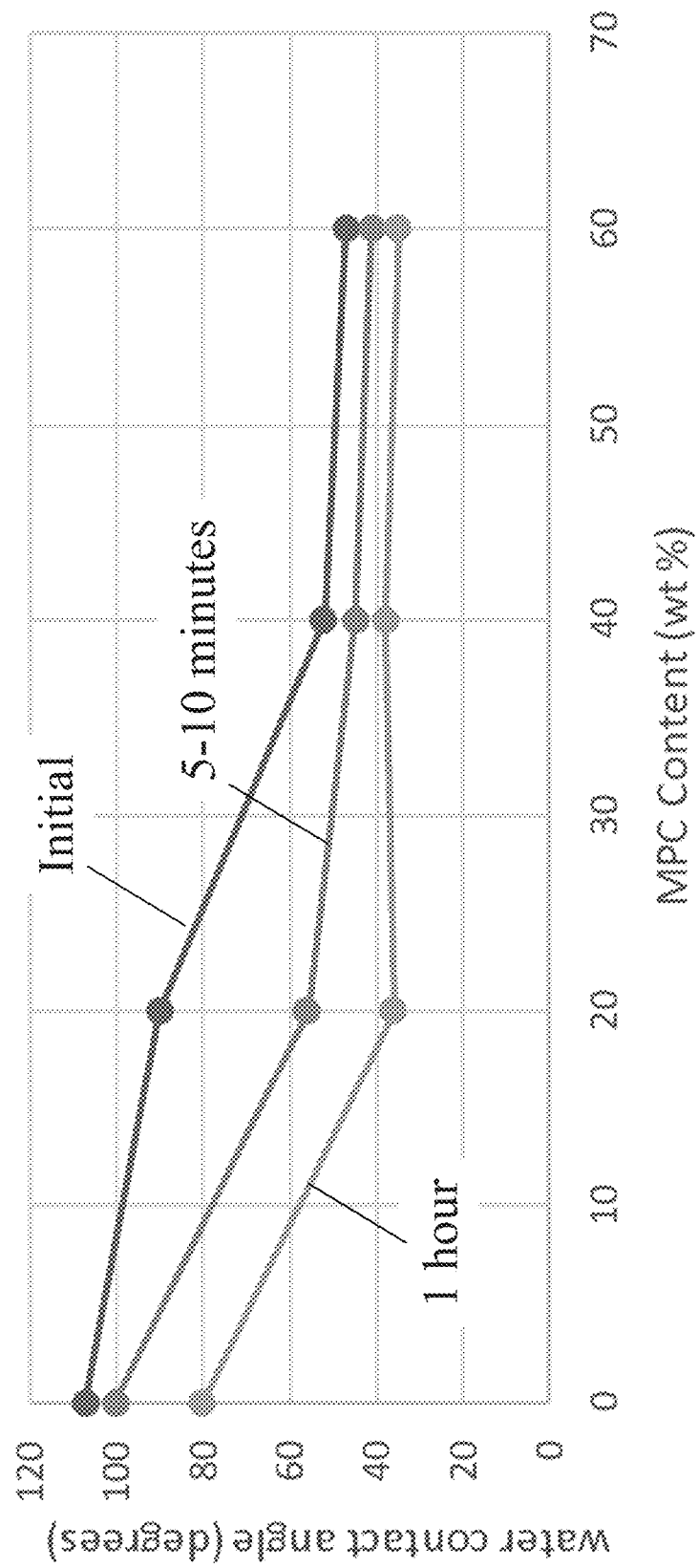
FIG. 4 is a plot showing Change in Contact Angle vs MPC Content without a primed substrate for a number of coatings produced in accordance with an aspect of the present invention.

Two sets of lenses were prepared by dip coating. Lenses were dipped in the polymer solution and dried at 60° C. for 2-3 h. Alternatively, the lenses were first dipped into a 2 wt % aqueous solution of the aziridine based primer, dried for 2-3 h at 60° C., coated by dipping into one of the polymer solutions and drying one final time at 60° C. The coatings were clear. Water contact angles were used to compare the samples. The results are shown in FIG. 4 which shows a decrease in water contact angle with increasing MPC content on the lenses.

The water contact angle decreased with all the coatings. The contact angle decrease was larger for higher MPC content, indicating better wetting of the lens. The uncoated lens started at 108° and decreased to 100 after about 10 minutes. The angle decreased further to 80° after about 1 hour.

Placing the 20% MPC polymer (Example 1) on the lens reduced the contact angle immediately to 90°, but the 40 and 60 wt % MPC (Examples 2 and 3, respectively) coatings gave better wetting as seen by the large reduction in contact angles. The higher content coatings were not as affected by time but showed good wetting immediately. Lens curvature was about 34 degrees, indicating a lower limit for wetting.

Figure 5:
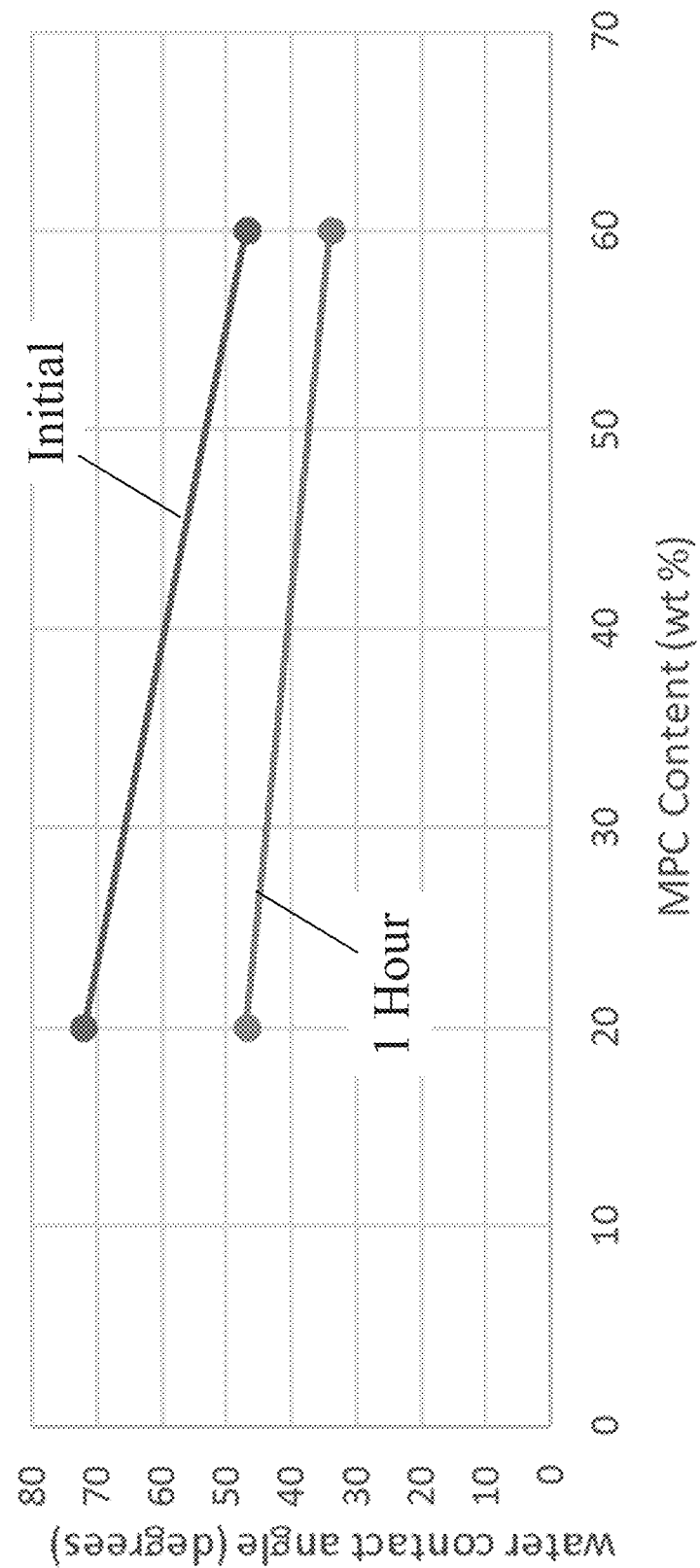
FIG. 5 is a plot showing Change in Contact Angle vs MPC Content with a primed substrate for a number of coatings produced in accordance with another aspect of the present invention.

Measurement of the water contact angle was made on the 20% and 60% MPC coatings on top of the aziridine based primer (FIG. 5). The 40% MPC coating was of poor quality and not reported. The polymer with 60 wt % MPC had a lower initial contact angle and a lower angle after an hour, again indicating the higher MPC content gave better wetting. It also appeared the coatings on the aziridine based primer had better wet mechanical integrity than the coatings without primer. This would be consistent with the aziridine ring reacting with the acrylic acid functionality to crosslink the MPC polymer. As shown in FIG. 5, water contact angle decreases with increasing MPC content on the aziridine based primer on the lenses.

NMR Characterization of 60% MPC Polymer (Example 3)

Figure 6:
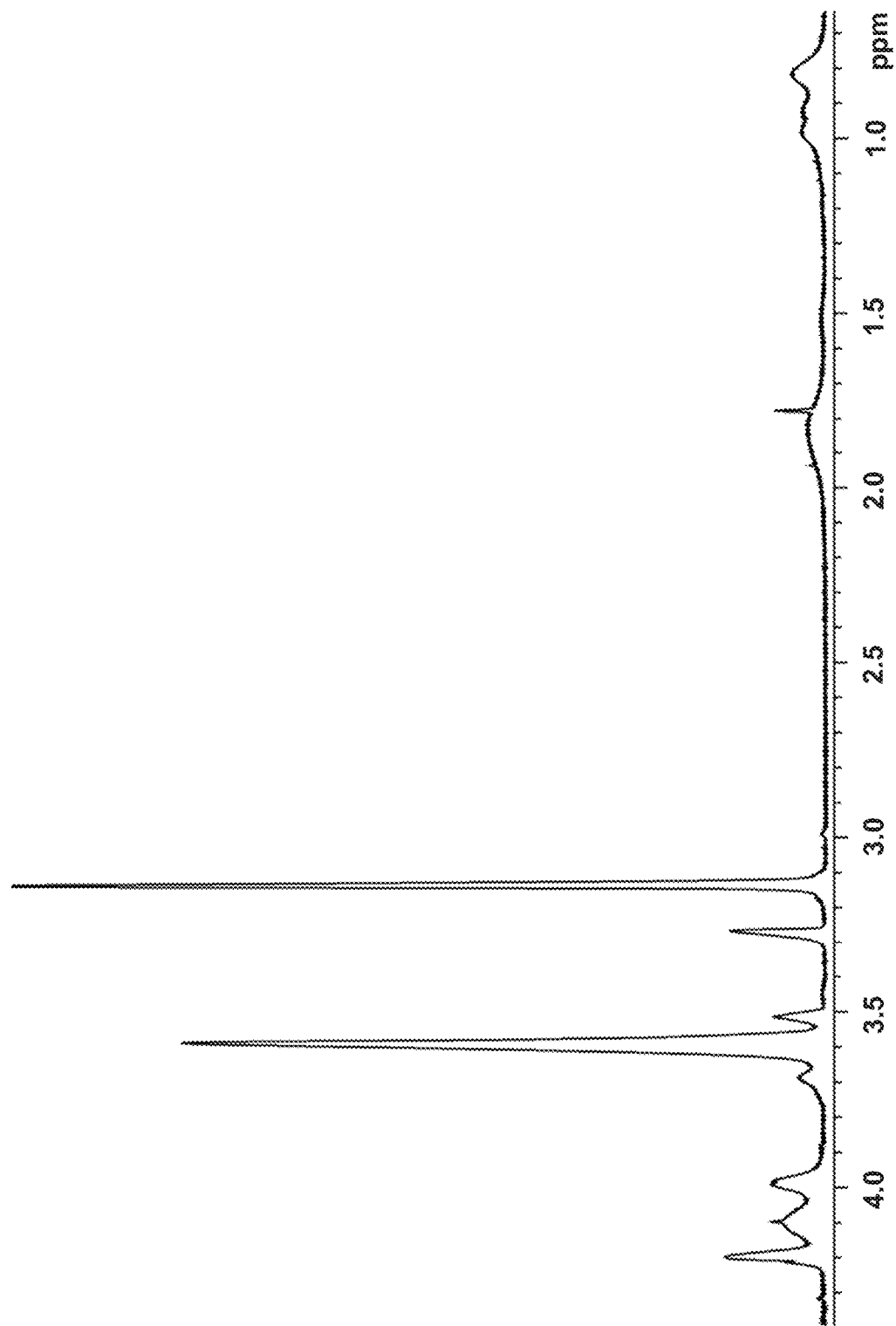
FIG. 6 is a 1H NMR (500 MHz) spectrum of a 60% MPC content polymer produced in accordance with an aspect of the present invention.

The sample was dissolved at a concentration of approx. 25 mg in 1 mL $D_2O$. As shown in FIG. 6, 1H NMR (500 MHz) was used to determine the composition of the polymer from Example 3, made with approximately 60 wt % MPC and 40 wt % PEG and the balance of 5 wt % methacrylic acid. Reference sample of MPC monomer CAS #67881-98-5, MAPEG monomer CAS #26915-72-0 and Methacrylic acid were run as a reference for chemical shifts. The-methacrylic acid monomer CAS #79-41-4 is too a low a level to detect in the NMR spectrum.

| Results | mole % | wt % |
|---------|--------|------|
| PEO     | 30     | 42   |
| MPC     | 70     | 58   |

Figure 7:
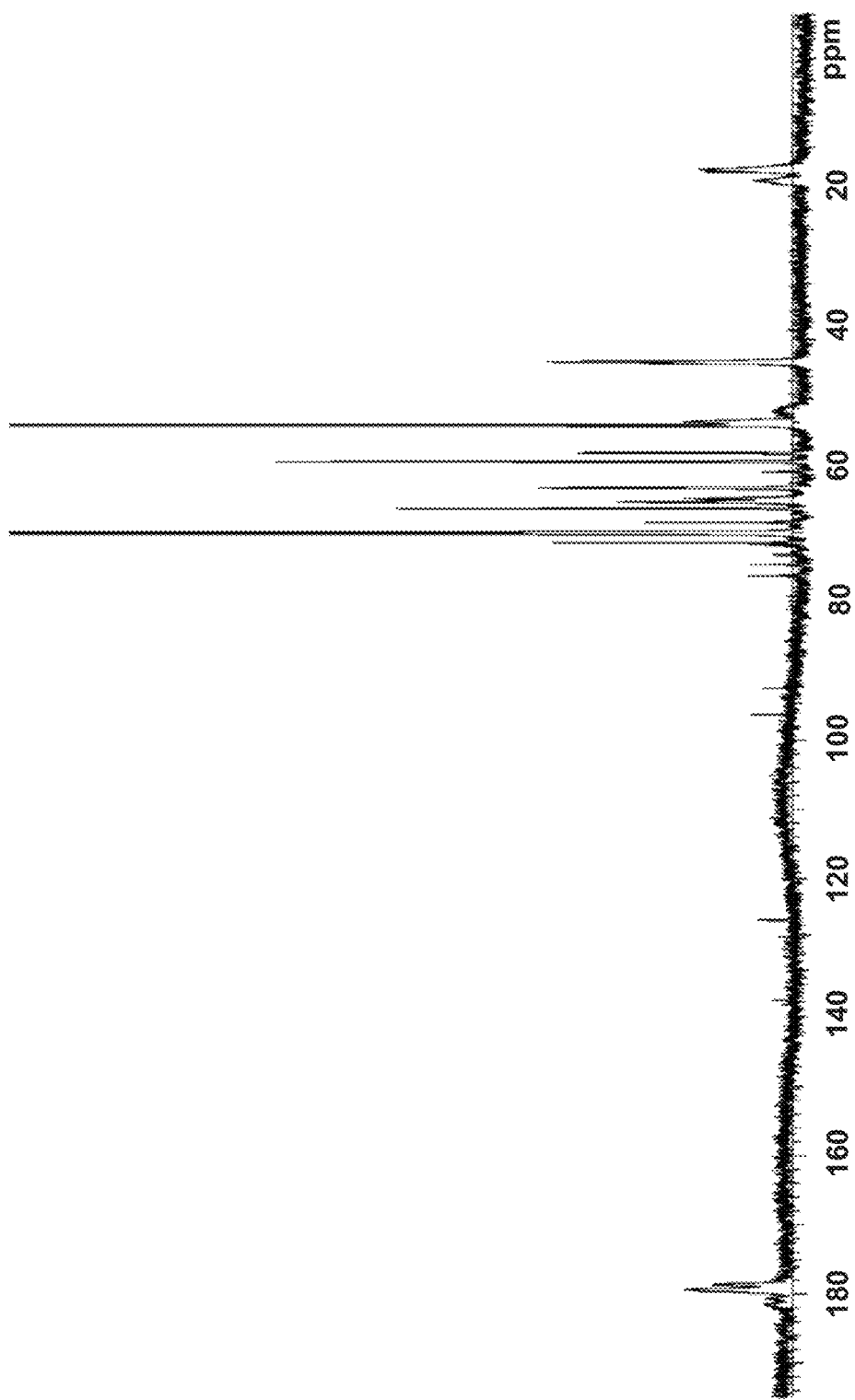
FIG. 7 is a 13C NMR (125 MHz) spectrum of a 60% MPC content polymer produced in accordance with an aspect of the present invention.
Figure 8:
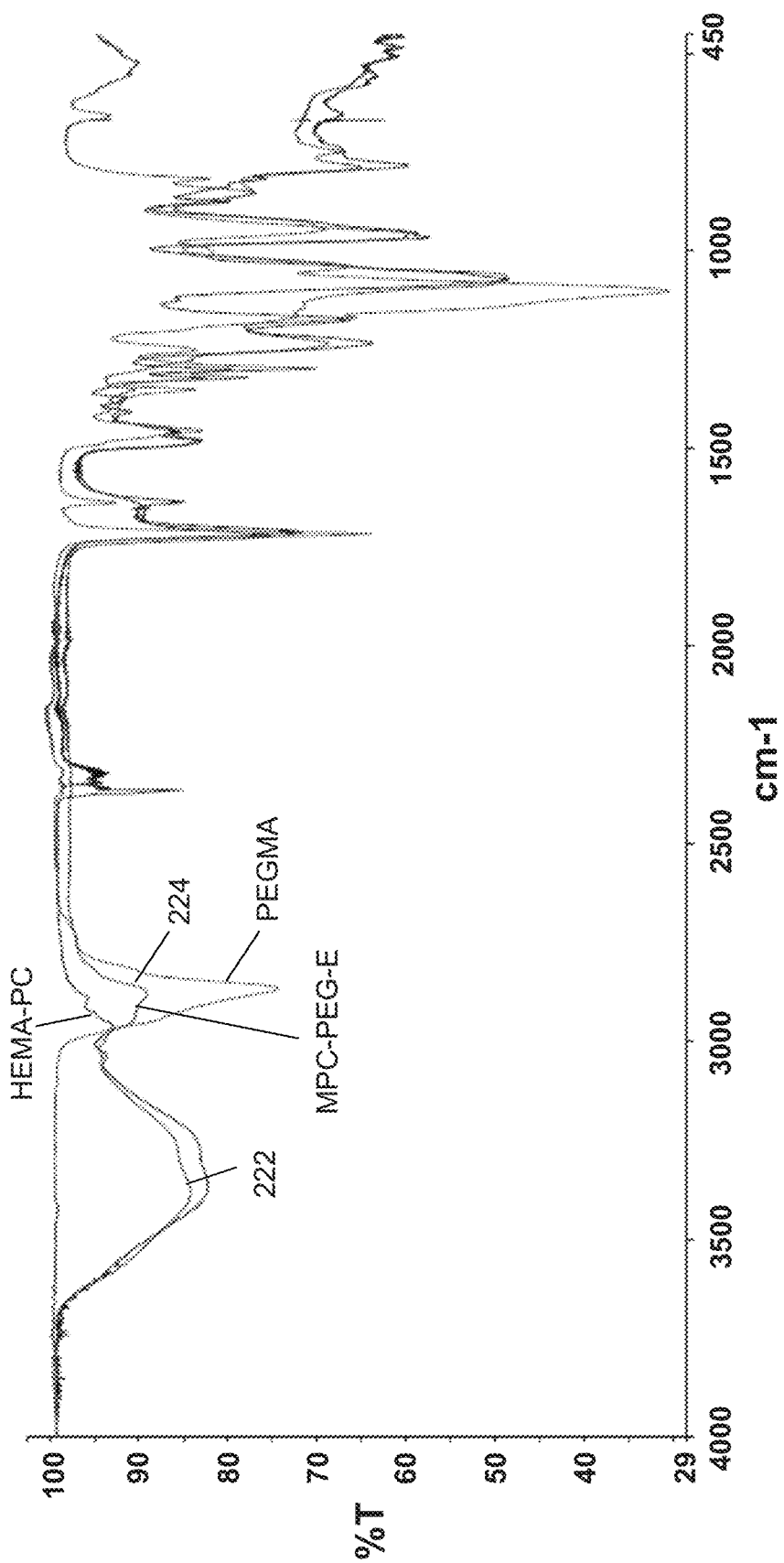
FIG. 8 is an FT-IR (Fourier Transform Infrared) spectrum of the 60% MPC content polymer shown in FIG. 6 and FIG. 7.

The 13C NMR spectrum is shown in FIG. 7.

Fourier Transformed Infra-Red Spectrum for the 60 MPC Polymer (Example 3) Along with the Two Monomer Spectra for MPC and MAPEG As shown in FIG. 7, the polymer displays both the zwitterion stretch 222 centered about 3400 $cm^{-1}$ observed for the MPC functionality as well as the C—H stretch 224 centered at about 2900 $cm^{-1}$ observed for the PEG functionality. Neither of the monomers displays both of the infra-red bands observed for the polymer. Thus, the infra-red spectrum showing how the 60% MPC polymer (Example 3) is made up of the two acrylates containing the MPC and the PEG functionality.

From the foregoing, it will be seen that this invention is one well adapted to attain all the ends and objects hereinabove set forth together with other advantages which are obvious and which are inherent to the method and apparatus. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. As used herein, the terms "having" and/or "including" and other terms of inclusion are terms indicative of inclusion rather than requirement.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed is:

1. A method of preparing a biocompatible polymeric coating comprising:
   a) preparing an aqueous polymer solution by contacting and reacting:
      i) methacrylic acid (MAA),
      ii) methacryloyloxyethyl phosphorylcholine (MPC), and
      iii) at least one methacrylate selected from the list consisting of hydroxyethyl methacrylate (HEMA), poly(ethylene glycol) monomethacrylate (PEGMA), and poly(ethylene glycol) methyl ether methacrylate (MAPEG), wherein a weight percent of MPC is at least 60%;
   b) precipitating a reaction product within the aqueous polymer solution by addition of acetone to produce a clear solid polymer material;
   c) dissolving the clear solid polymer material in an alcohol or water to produce a purified polymer solution;
   d) preparing an aqueous polyaziridine coupling agent solution; and
   e) mixing the purified polymer solution with the coupling agent solution to form the biocompatible polymeric coating.

2. A method of applying a biocompatible polymeric coating to a substrate surface, the method comprising:
   A) preparing the biocompatible polymeric coating in accordance with claim 1; and
   B) contacting and reacting the coating solution with the substrate surface to coat the surface with the biocompatible polymeric coating.

3. The method of claim 2 further comprises:
   C) loading the polymer solution in a first syringe prior to the mixing step; and
   D) loading the coupling agent solution in a second syringe prior to the mixing step,
   wherein the mixing step includes dispensing a first volume of polymer solution from the first syringe and dispensing a second volume of coupling agent solution from the second syringe.

4. The method of claim 3 wherein the first syringe and the second syringe comprise a dual cartridge syringe.

5. The method of claim 3 wherein the first volume is the same as the second volume.

6. The method of claim 2 wherein a therapeutic agent solution is further added during at least one of steps A) and B).

7. The method of claim 2 further comprising:

C) pretreating the substrate surface to functionalize the substrate surface for reactivity with aqueous coupling agent solution and/or coating solution, wherein step C) occurs prior to step B).

8. A method of applying a biocompatible polymeric coating to a substrate surface, the method comprising:

a) preparing an aqueous polymer solution by contacting and reacting:
  i) methacrylic acid (MAA),
  ii) methacryloyloxyethyl phosphorylcholine (MPC), and
  ii) at least one methacrylate selected from the list consisting of hydroxyethyl methacrylate (HEMA), poly(ethylene glycol) monomethacrylate (PEGMA), and poly(ethylene glycol) methyl ether methacrylate (MAPEG), wherein a weight percent of MPC is at least 60%;

b) precipitating a reaction product within the aqueous polymer solution by addition of acetone to produce a clear solid polymer material;

c) dissolving the clear solid polymer material in an alcohol or water to produce a purified polymer solution;

d) preparing an aqueous polyaziridine coupling agent solution;

e) contacting and reacting the aqueous coupling agent solution with the substrate surface to form a primed substrate surface; and f) contacting and reacting the aqueous polymer solution with the primed substrate surface to coat the surface with the biocompatible polymeric coating.

9. The method of claim 8 further comprising:

g) pretreating the substrate surface to functionalize the substrate surface for reactivity with the aqueous coupling agent solution, wherein step g) occurs prior to step e).

* * * * *